United States Patent [19]

Schmitt et al.

[11] Patent Number: 4,485,026
[45] Date of Patent: Nov. 27, 1984

[54] HARD WATER STABILITY IMPROVERS FOR OIL-IN-WATER EMULSIONS HYDRAULIC FLUIDS

[75] Inventors: Kirk D. Schmitt, Pennington; Joosup Shim, Wenonah, both of N.J.

[73] Assignee: Mobil Oil Corporation, New York, N.Y.

[21] Appl. No.: 430,457

[22] Filed: Sep. 30, 1982

[51] Int. Cl.$^3$ .......................... C10M 3/04; C10M 3/34
[52] U.S. Cl. .................................... 252/78.1; 252/41; 252/49.5; 252/52 A; 252/75; 252/549; 252/558; 260/513 R
[58] Field of Search ............... 252/75, 78.1, 549, 558, 252/41, 49.5, 52 A; 260/513 R

[56] References Cited

U.S. PATENT DOCUMENTS

| 3,639,277 | 1/1972 | Poettmann et al. | 252/75 |
| 4,096,175 | 6/1978 | Naylor et al. | 260/513 R |
| 4,257,902 | 3/1981 | Singer | 252/75 |

*Primary Examiner*—Paul Lieberman
*Assistant Examiner*—Robert A. Wax
*Attorney, Agent, or Firm*—Alexander J. McKillop; Michael G. Gilman; Howard M. Flournoy

[57] ABSTRACT

Lubricating oils which in aqueous media are highly useful as, for example, hydraulic fluids, are provided having improved hard water stability characteristics when oil soluble alkylphenoxypolyethoxylated sulfonates are added thereto.

11 Claims, No Drawings

HARD WATER STABILITY IMPROVERS FOR OIL-IN-WATER EMULSIONS HYDRAULIC FLUIDS

BACKGROUND OF THE INVENTION

1. Field of the Invention

This invention relates to lubricating oils, and particularly to oils suitable for admixing with water to form hydraulic fluids and the like and to aqueous lubricant systems having improved hard water stability characteristics. The invention is even more particularly concerned with fire resistant hydraulic fluids incorporating oil soluble alkylphenoxypolyethoxylated sulfonates as the stability improvers.

2. Discussion of the Prior Art

With the increasing use of hydraulic fluids and similar lubricants, more and more use of oil-in-water emulsion fluids as lubricants in many industrial applications, as for example, hydraulic fluids, is well known. In these fluids, water is the continuous phase and the "oil" is in the dispersed phase. The term oil is not limited in this particular art to its usual meaning but may include non-oil components such as chemical additives to the exclusion of the oil in the dispersed phase.

High content water fluids (HWCF) of the type disclosed herein are usually prepared with various ratios of soft (distilled) water and oil or chemical concentrates. Many of the fluids, however, are unstable if modified, or if unmodified, natural water instead of soft water is used. The stability of HWCF fluids is further affected by the ionic activity of salts present in hard water. Chelating agents have been used in the prior art as one means to overcome this problem. A new emulsifier system has now been developed which makes it possible for high water content fluids to remain stable in the most severe hard water systems.

Propane sulfonates of various amines and polyethoxylated alcohols are known surfactants or surface active agents having a special usefulness in tertiary oil recovery processes. With the increasing use of functional fluids such as hydraulic fluids and more and more sophisticated machine systems that demand closer tolerances to perform new and more difficult functions, there is a critical need for stability improvers for oil-in-water fluids; however, to the best of applicants' knowledge and belief, the HWCF fluid compositions disclosed herein are novel and are heretofore unknown.

SUMMARY OF THE INVENTION

In accordance with the invention, there is provided an emulsifiable lubricant composition and more particularly, there is provided an oil-in-water emulsion fire-resistant hydraulic fluid comprising a high water content base fluid and an effective amount of an oil soluble alkylphenoxypolyethoxylated sulfonate sufficient to improve the hard water stability characteristics of the fluid thereby allowing fluids containing it to remain stable under the severest hard water conditions. The unique combination of emulsifier/stabilizer systems already present in base HWCF fluids (see Table 1 for example) and the alkylphenoxypolyethoxylated sulfonates described herein provide the improved performance characteristics desired.

DESCRIPTION OF PREFERRED EMBODIMENTS

The fluids disclosed herein may contain from about 0.1 to about 10% by weight, and preferably as little as from about 0.2 to about 3% by weight of the base lubricant fluid based on the weight of the total composition. Typically a fluid, in accordance with this invention, will broadly comprise from about 40 to about 99% by weight water, and preferably from about 95 to about 98% by weight based on the weight of the total composition. The remainder of the fluid will comprise the base lubricant oil.

The high water content fluids disclosed herein are not restricted to the specific compositions and percentages set forth herein. See Table 1 below for the composition of a highly suitable base oil stock. Further, any number of suitable additive materials may be also utilized in these fluids for their known purposes without detrimental effect.

TABLE 1

| Composition of Base HWCF Fluid (Example 1) | | |
|---|---|---|
| Chemical Type | Function | % Wt. |
| Solvent Naphthenic Neutral | Lubricant | 39.0 |
| Zinc dialkyl dithiophosphate | Antiwear | 10.0 |
| Calcium nonylnaphthalene sulfonate | Rust inhibitor | 5.0 |
| Isopropyl amino ethanol | Vapor phase rust-inhibitor | 1.0 |
| Polyethoxylated soyamine | Emulsifier | 25.0 |
| Potassium soap of rosin | Emulsifier/Stabilizer | 20.0 |

The alkylphenoxyethoxylated sulfonates of the invention have the general formula:

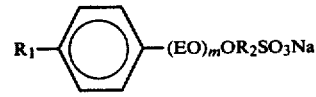

wherein $R_1$ and $R_2$ are $C_1$ to $C_{36}$ alkyl and may be the same or different, and m is any number, fractional or whole, from 3 to about 24.

The propane sulfonates embodied herein may be prepared in any convenient manner. One method is the reaction of alkali metal salts of the alcohols or thiols with propane sultone, which is a convenient high-yield laboratory synthesis but which is not desirable on a large scale. Propane sultone is expensive to purify and is a known carcinogen requiring expensive controls to minimize exposure to it. Nevertheless, a typical preparative method for the alkylphenoxypolyethoxylated propane sulfonates may be as follows: alkylphenoxypolyethoxyethanol is reacted with metallic sodium in the presence of a suitable solvent such as toluene for about 2 to 4 days. The reaction mixture is then cooled and the propane sultone added thereto. After about 3 to 6 hours, the mixture is processed for recovery of the desired product. See, for example, U.S. Pat. No. 3,888,917 which relates to another method of preparing organic sulfonates by sulfide addition to unsaturated hydrocarbons. Any suitable method may be used.

The following examples are merely illustrative of a preferred embodiment and it should not be construed as a limitation on the invention.

EXAMPLE 2

A mixture of 100 grams of commercially available nonylphenoxypolyethoxyethanol and 220 ml toluene degassed via three cycles of a Firestone valve, refluxed until dry through a Dean-Stark trap, and reacted at reflux with 4.74 grams of sodium for three days. The mixture was then cooled to 30° C. and 25.1 grams freshly distilled propane sultone in 25 ml of toluene added over a period of 30 minutes. After four hours, the mixture was stripped in a freeze-dry flask on a rotary evaporator, then dried to a constant weight at 70° C./0.1 mm of mercury to give 127.3 grams. Integration of the C-13 NMR peak at 60.5 ppm ($CH_2OH$) versus the peak at 48.3 ppm ($CH_2SO_3{}^-$) indicated 5.0 mole percent unreacted alcohol and confirmed that the desired product, having an m value of 4.2, was obtained.

EXAMPLE 3

Additional nonylphenoxypolyethoxylenephenoxy propane sulfonate was prepared in an identical manner to that of Example 2, and the desired product recovered except that the ethyleneoxy moiety in Example 3 had an m value of 5.6, instead of an m value of 4.2 for the ethyleneoxy moiety as in Example 2.

EXAMPLE 4

A di-nonylphenoxypolyethyleneoxy propane sulfonate was prepared in an identical manner to that of Example 2.

EVALUATION

The products of Examples 2, 3 and 4 were each separately admixed with the base fluid described as Example 1 in Table 1 and subjected to the United Kingdom National Coal Board (NCB) #19 Hard Water Stability Test. The results from this evaluation are set forth in Table 2. The data is in weight percent based on the weight of base lubricant fluid, Example 7.

As will be noted, the representative prior art fluid Example 1 (described in Table 1) contains a nonionic stabilizer emulsion package. However, this does not provide sufficient stability for the compositions to pass the hard water stability test. On the other hand, the stability effect of the additives in accordance with this invention provide all the performance characteristics required for the severe hard water stability requirements of the U.K. NCB #19 Hard Water Stability Test. The additives of the present invention are intended to enhance and supplement emulsifiers normally used in prior art formulations. The data set forth in Table 2 clearly disclose that the intended purpose is accomplished.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

We claim:

1. A fire resistant lubricant composition comprising an emulsifiable high water content base fluid and an effective amount of an oil-soluble $C_1$ to $C_{36}$ alkylphenoxypolyethoxylated sulfonate having the following general formula

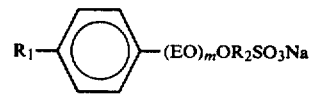

wherein $R_1$ and $R_2$ are $C_1$ to $C_{36}$ alkyl and may be the same or different, and m is any number, fractional or whole, from 3 to about 24, or mixtures thereof.

2. The composition of claim 1 wherein $R_1$ of said ethoxylated sulfonate is $C_9$ and $R_2$ of said ethoxylated sulfonate is $C_3$.

TABLE 2

| | Hard-Water Stability Data | | | |
|---|---|---|---|---|
| | Example 1 | Example 2 | Example 3 | Example 4 |
| Example 1 | 3.0 | 3.0 | 3.0 | 3.0 |
| $C_9$—⌬—$(EO)_{4.2}$—$OC_3H_6SO_3Na$ (Example 2) | — | 0.2 | — | — |
| $C_9$—⌬—$(EO)_{5.6}$—$OC_3H_6SO_3Na$ (Example 3) | — | — | 0.2 | — |
| $(C_9)_2$—⌬—$(EO)_{6.5}$—$OC_3H_6SO_3Na$ (Example 4) | — | — | — | 0.2 |
| Water | 97.0 | 96.8 | 96.8 | 96.8 |
| NCB #19 Hard Water Stability (70° C., 168 hours) | FAIL | BORDERLINE PASS | PASS | FAIL |

The test as indicated was conducted at 70° C. over a period of 168 hours. Compositions containing the additives in accordance with this invention were compared in the test with a composition comprising the base fluid and water.

3. The composition of claim 1 or 2 where m of said ethoxylated sulfonate is 5.6.

4. The composition of claim 1 wherein the composition contains from about 1 to about 5 weight % of base oil based on the weight of the total composition.

5. The composition of claim 1 wherein the composition contains from about 0.1 to about 10 weight % of a propane ethoxylated sulfonate as described therein based on the weight of the total composition.

6. The composition of claim 1 wherein the base fluid contains from about 10 to about 50 weight % of a polyethoxylated soyamine emulsifier and from about 10 to about 40 weight % of a potassium soap rosin emulsifier/stabilizer based on the weight of the total composition.

7. The composition of claim 1 wherein the high water content base fluid contains from about 40 to about 99 weight % water based on the weight of the total composition.

8. The composition of claim 4 wherein said oil comprises an oil of lubricating viscosity selected from mineral oils, synthetic oils or mixtures thereof.

9. The composition of claim 8 wherein the oil of lubricating viscosity is a mineral oil.

10. The composition of claim 1 wherein said composition is a hydraulic fluid.

11. A product as described in claim 1 comprising said oil-soluble $C_1$ to $C_{36}$ alkylphenoxypolyethoxylated sulfonate wherein said fluid consists essentially of a mixture comprising an oil of lubricating viscosity, a zinc dihydrocarbyldithiophosphate, a hydroxyl-containing alkylamine having from about 2 to about 100 carbon atoms, a polyethoxylated soyamine, an alkali metal rosin soap and an alkali metal alkylnaphthalene sulfonate.

* * * * *